(12) United States Patent
Kim et al.

(10) Patent No.: US 11,246,901 B2
(45) Date of Patent: Feb. 15, 2022

(54) BLACK RICE SPROUTING LIQUID HAVING ANTI-INFLAMMATORY EFFECT AND MANUFACTURING METHOD THEREOF

(71) Applicants: WELLBEINGGO CO., LTD., Gyeongsan-si (KR); Sung Hyun Kim, Daegu (KR)

(72) Inventors: Sung Hyun Kim, Daegu (KR); Jung Ae Jun, Daegu (KR)

(73) Assignees: WELLBEINGGO CO., LTD., Gyeongsan-si (KR); Sung Hyun Kim, Daegu (KR)

( * ) Notice: Subject to any disclaimer, the term of this patent is extended or adjusted under 35 U.S.C. 154(b) by 147 days.

(21) Appl. No.: 16/359,572

(22) Filed: Mar. 20, 2019

(65) Prior Publication Data
US 2019/0290716 A1    Sep. 26, 2019

(30) Foreign Application Priority Data
Mar. 20, 2018    (KR) ........................ 10-2018-0031987

(51) Int. Cl.
A61K 36/899 (2006.01)
A61P 29/00 (2006.01)
A61K 45/06 (2006.01)

(52) U.S. Cl.
CPC ............ A61K 36/899 (2013.01); A61K 45/06 (2013.01); A61P 29/00 (2018.01)

(58) Field of Classification Search
CPC ........ A61K 36/899; A61K 45/06; A61P 29/00
See application file for complete search history.

(56) References Cited

FOREIGN PATENT DOCUMENTS

| JP | 2000-093097 A | | 4/2000 |
|----|----|----|----|
| JP | 2000093097 A | * | 4/2000 |
| KR | 2000-0075359 A | | 12/2000 |
| KR | 20000075379 A | * | 12/2000 |
| KR | 2001-0105020 A | | 11/2001 |
| KR | 2002-0042384 A | | 6/2002 |
| KR | 2002-0092334 A | | 12/2002 |

OTHER PUBLICATIONS

Aggarwal, B.B., et al., "Inflammation and cancer: How hot is the link," Biochemical Pharmacology, vol. 72, pp. 1605-1621 (2006).
Chandrasekaran, M., and Venkatesalu, V., "Antibacterial and antifungal activity of Syzygium jambolanum seeds," Journal of Ethnopharmacology, vol. 91, Issue 1, pp. 105-108 (Mar. 2004).
Dagne J.M., et al., "Coxibs and Cardiovascular side-effects: from light to shadow," Current Pharmaceutical Design, vol. 12, Issue 8, pp. 971-975 (2006).
Guha, M., and Mackman N., "LPS induction of gene expression in human monocytes," Cellular Signalling, vol. 13, Issue 2, pp. 85-94 (Feb. 2001).
Hyun EA, "Anti-inflammatory effect of Salvia officinalis," L. extract. Cheju National University Korea (2003).
Makins, R., and Ballinger, A., "Gastrointestinal side effects of drugs," Expert Opinion on Drug Safety, vol. 2, Issue 4, pp. 421-429 (Jul. 2003).
Masferrer, J.L., et al., "Selective inhibition of inducible cyclooxygenase 2 in vivo is antiinflammatory and nonulcerogenic," Proceedings of the National Academy of Sciences of the United States of America, vol. 91, pp. 3228-3232 (Apr. 1994).
Nishida, T., et al., "Geranylgeranylacetone induces cyclooxygenase-2 expression in cultured rat gastric epithelial cells through NF-kB," Digestive Diseases and Sciences, vol. 52, pp. 1890-1896 (2007).
Seibert, K., "Pharmacological and biochemical demonstration of the role of cyclooxygenase 2 in inflammation and pain," Proceedings of the National Academy of Sciences of the United States of America, vol. 91, pp. 12013-12017 (Dec. 1994).
Vane, R.J., et al., "Cyclooxygenases 1 and 2," Annual Review of Pharmacology and Toxicology, vol. 38, pp. 97-120 (1998).
Zamora, R., et al., "Inducible nitric oxide synthase and inflammatory diseases," Molecular Medicine, vol. 6, Issue 5, pp. 347-373 (2000).

* cited by examiner

Primary Examiner — Aaron J Kosar
(74) Attorney, Agent, or Firm — Maschoff Brennan (57) ABSTRACT

Disclosed are a black rice sprouting liquid having an excellent anti-inflammatory effect through low-temperature treatment and room-temperature treatment of water used when black rice is sprouted, and a manufacturing method of the black rice sprouting liquid. The black rice sprouting liquid is obtained by performing low-temperature treatment on water used when black rice is sprouted in an open container at a temperature ranging from 1° C. to 5° C. for 1 day to 10 days, and then performing room-temperature treatment on the resulting water in the open container at a temperature ranging from 10° C. to 30° C. for 30 days to 210 days.

4 Claims, 7 Drawing Sheets

FIG. 1

| | Document Identification No.: S005-VKJE-JOAU-TJPX |
|---|---|
| TEST AND INSPECTION REPORT | |

| ISSUE NO. | | REGISTRATION NO. | |
|---|---|---|---|
| TEST COMPLETION DATE | | REGISTRATION DATE | |
| PRODUCT NAME | BLACK RICE SPROUTING LIQUID (SAMPLE) | | |
| TYPE MATERIAL ITEM NAME | OTHER CRITERIA AND STANDARDS, ETC. | | |
| MANUFACTURING (IMPORT) DATE | | DISTRIBUTION (QUALITY MAINTENANCE) PERIOD | |
| APPLICANT | FULL NAME | SUNGHYUN KIM | COMPANY NAME | WELL-BEING GO CO., LTD |
| | ADDRESS | 50 GAMASIL-GIL, HAYING-EUP, GYEONGSAN-SI, GYEONGSANGBUK-DO, KOREA (ROOM # 202, SECOND FLOOR, R&DB CENTER, KYUNGIL UNIVERSITY, GYEONGBUK TECHNOPARK) | | |
| MANUFACTURER | COMPANY NAME | | COUNTRY OF MANUFACTURE | |
| | ADDRESS | | | |
| TEST AND INSPECTION PURPOSE | FOOD/OTHERS (FOR REFERENCE) | | |

| TEST AND INSPECTION ITEMS AND RESULTS | | | | |
|---|---|---|---|---|
| TEST AND INSPECTION ITEMS AND RESULTS | TEST AND INSPECTION CRITERIA | TEST AND INSPECTION RESULTS | ASSESSMENT | REMARKS |
| LEAD | NO REFERENCE | NOT DETECTED | THE TEST CONFIRMED | |
| NUMBER OF BACTERIA | NO REFERENCE | 32000000,87 000000,7800 0000 960000 00,74000000 | THE TEST CONFIRMED | |
| E. COLI GROUP | NO REFERENCE | 1100000,140 000,110000 0,36000000,99 0000 | THE TEST CONFIRMED | |

OVERALL ASSESSMENT: THE TEST CONFIRMED
TEST INSPECTOR: NAYOUNG LEE, EUNAE JEON
TEST AND INSPECTION MANAGER: KYUDEOK PARK
NOTE:
* THE ABOVE ASSESSMENTS ARE ONLY FOR THE REQUESTED TEST AND INSPECTION ITEMS
* IF THERE IS NOT ENOUGH SPACE IN DOCUMENT, TEST AND INSPECTION ITEMS AND RESULTS CAN BE PROVIDED IN APPENDIX
* FOR ADVERTISEMENT OF TEST RESULTS OR DISPLAY OF TEST RESULTS ON CONTAINER, PACKAGING, ETC., THE WHOLE CONTENT OF THE TEST AND INSPECTION REPORT MUST BE PROVIDED.

MARCH 13, 2018

BK LABORATORY CO., LTD

GEUMSAMRO 585, GEUMJEONG-GU, BUSAN (DASOL BUILDING 4TH AND 5TH FLOOR, NAMSAN-DONG

FIG. 2

KOREA RESEARCH & INSTITUTE OF BIO MEDICAL SCIENCE
KOREA RESEARCH & INSTITUTE OF BIO MEDICAL SCIENCE BUILDING, 6, DAEHEUNG-RO 28-GIL, JUNG-GU, DAEJEON, SOUTH KOREA

TEST REPORT
Report No.: LRIBS18-016.001
ISSUE DATE: 2018. 2. 5.
APPLICANT: WELL-BEING GO CO., LTD
NUMBER OF SAMPLES: 1
SAMPLE NAME: BROWN RICE SPROUTING LIQUID
TEST ITEM: ASSAY FOR NUMBER OF LIVE BACTERIA FOR IDENTIFICATION Result

| sample | general bacteria | Fungi(Yeast) |
|---|---|---|
| BROWN RICE SPROUTING LIQUID | $6.8 \times 10^6$ | $3.2 \times 10^4$ |
| Remarks | three types | three types |

ANNOTATION) - cfu: colony forming unit
           - Saple was diluted with sterile water
NOTE.
1. The test report shows test results of the samples submitted by the applicant and is forbidden to be used for purposes other than those stated herein.
2. The test report cannot be used for publicity, advertisement, and litigation without the prior written consent of THE KOREA RESEARCH & INSTITUTE OF BIO MEDICAL SCIENCE.

DIRECTOR OF KOREA RESEARCH & INSTITUTE OF BIO MEDICAL SCIENCE
KOREA RESEARCH & INSTITUTE OF BIO MEDICAL SCIENCE BUILDING, 6, DAEHEUNG-RO 28-GIL, JUNG-GU, DAEJEON, SOUTH KOREA

FIG. 3

KOREA RESEARCH & INSTITUTE OF BIO MEDICAL SCIENCE
KOREA RESEARCH & INSTITUTE OF BIO MEDICAL SCIENCE BUILDING, 6, DAEHEUNG-RO 28-GIL, JUNG-GU, DAEJEON, SOUTH KOREA

TEST REPORT

Report No.: 2018KRIBS-389.001
ISSUE DATE: 2018. 3. 7.
APPLICANT: WELL-BEING GO CO., LTD
NUMBER OF SAMPLES: 1
SAMPLE NAME: Black rice sprouting liquid
TEST ITEM: MICROORGANISM IDENTIFICATION Result

| SAMPLE NAME | IDENTIFICATION RESULTS |
|---|---|
| BACTERIUM 1 | *Citrobacter murliniae* 99% homology |
| BACTERIUM 2 | *Pseudacidovorax intermedius* 99% homology |
| BACTERIUM 3 | *Paenirhodobacter enshiensis* 99% homology |
| FUNGUS 1 | *Candida intermedia* 99% homology |
| FUNGUS 2 | *Candida tropicalis* 98% homology |
| FUNGUS 3 | *Meyerozyma sp.* 99% homology |

* For details please see attached pages

NOTE.
1. The test report shows test results of the samples submitted by the applicant and is forbidden to be used for purposes other than those stated herein.
2. The test report cannot be used for publicity, advertisement, and litigation without the prior written consent of THE KOREA RESEARCH & INSTITUTE OF BIO MEDICAL SCIENCE

DIRECTOR OF KOREA RESEARCH & INSTITUTE OF BIO MEDICAL SCIENCE
KOREA RESEARCH & INSTITUTE OF BIO MEDICAL SCIENCE BUILDING, 6, DAEHEUNG-RO 28-GIL, JUNG-GU, DAEJEON, SOUTH KOREA

BLACK RICE SPROUTING LIQUID HAVING ANTI-INFLAMMATORY EFFECT AND MANUFACTURING METHOD THEREOF

TECHNICAL FILED

The present invention relates to a manufacturing method of a black rice sprouting liquid having an anti-inflammatory effect and a black rice sprouting liquid obtained using the method, and more particularly to a black rice sprouting liquid having an excellent anti-inflammatory effect through low-temperature treatment and room-temperature treatment of water used when black rice is sprouted, and a manufacturing method of the black rice sprouting liquid.

PRIOR ART

Recently, it has been reported that wild plants also have substances capable of preventing or treating diseases, and studies have been actively conducted to search for substances having various physiological functions from various resources on the earth according to a cultural need to live a healthy life. Among these substances, especially compounds included in plant resources are receiving much attention.

Recently, due to aging and dietary intervention, acute inflammatory diseases and chronic inflammatory diseases such as rheumatoid arthritis, herpes zoster, and rhinitis have been increasing (Hyun E A. Anti-inflammatory effect of *Salvia officinalis* L. extract. Cheju National University. Korea 2003). Chronic inflammation occurs when materials that cause acute inflammation, such as tuberculosis bacilli, protozoa, fungi, other parasites that resist host defense and are capable of remaining in tissue for a long period of time, and the like are not removed. Onychomycosis, which is a fungal infection of fingernails or toenails, is also an inflammatory nail disease.

Inflammation is defined as a type of complex immune responses due to the innate immune system caused by harmful substances in biological tissue in which blood vessels are distributed, and is generally accompanied by heat and pain. That is, inflammation collectively refers to defensive responses that occur in the body when biological tissue is damaged, and the body responds to trauma, burns, or bacterial invasion, thus locally causing hyperemia, edema, fever, and pain. Inflammation responses are related to a step of reconstructing damaged tissues, and include all steps of removing microorganisms that damage tissues, causative substances such as toxins, cells and tissues that become necrotic as a result of damage, and the like.

Direct causes of inflammation responses include:
(1) Activation of complement system
(2) Secretion of inflammatory cytokines
(3) Fibrinolysis
(4) Extravasation and phagocytosis of white blood cells
(5) Coagulation
(6) Other inflammatory substances, and inflammation occurs by actions of immune cells and systems due to the above causes. Causes of these immune responses include factors that can cause any form of damage to tissue, and examples of external factors that can cause inflammation include:
(1) Physical causes: burns, frostbite, physical injury/trauma, foreign bodies, and ionizing radiation
(2) Biological causes: pathogens, hypersensitivity, and stress
(3) Chemical causes: toxins and alcohols.

As the correlation between chronic inflammation and cancer or other diseases has been reported, efforts have been made to reduce the risk of diseases by reducing inflammatory responses using dietary intervention (Aggarwal B B et al. Inflammation and cancer: How hot is the link 72: 1605-1621(2006)).

Inflammatory responses are one of the defense mechanisms of biological tissues against physical and chemical stimuli or bacterial infections from the external environment, and are a mechanism to recover or regenerate injured tissues (Zamora R, et al. Inducible nitric oxide synthase and inflammatory diseases. Mol. Med. 6: 347-373(2000)). When an inflammatory response occurs in the body, inflammatory cells such as macrophages secrete inflammatory mediators such as nitrogen monoxide (NO), prostaglandin E2 (PGE2), tumor necrosis factor-α (TNF-α), interleukin-1β (IL-1β), and the like (Guha M, Mackman N. LPS induction of gene expression in human monocytes. Cell Signal. 13: 85-94 (2001)). In normal cases, the living body neutralizes or eliminates causative factors through inflammatory responses, and regenerates injured tissues to recover a normal structure and function, otherwise a disease state such as chronic inflammation may proceed. Inflammatory responses are caused by various stimuli such as infectious agents, ischemia, antigen-antibody reactions, heat, other physical injuries, and the like, and clinical symptoms such as erythema, edema, tenderness, pain, and the like occur. Inflammatory responses occur in three different phases, each apparently mediated by different mechanisms: first, an acute transient phase characterized by local vasodilation and increased capillary permeability; second, a delayed, subacute phase characterized by infiltration of leukocytes and phagocytes; and third, a chronic proliferative phase, in which tissue degeneration and fibrosis occur. Many other mechanisms involve inflammatory responses.

It is known that inflammatory responses can be observed in almost all clinical diseases, and enzymes involved in inflammatory responses play an important role in carcinogenesis. Therefore, treatment of inflammatory diseases is one of the challenges of medical science today. Among these inflammatory diseases, there are bacterial diseases which can be fundamentally treated by antibiotics, but most cases are known as intractable diseases that have no specific treatment methods, because they are caused by tissue damage due to autoimmune responses.

The anti-inflammatory effects of most non-steroidal anti-inflammatory drugs (NSAIDs) are mediated by inhibiting COX enzymatic activity (Vane et al., Annual Review of Pharmacology and Toxicology, 38:97-120, 1998).

COX-1, which is an enzyme present constantly in tissues such as the stomach or kidneys, is involved in maintaining normal homeostasis, whereas COX-2 is transiently and rapidly expressed in cells by mitogens or cytokines during inflammation or other immune responses. NSAIDs used in the treatment of chronic inflammatory diseases such as acute or rheumatoid arthritis are known to exhibit side effects such as gastrointestinal disorders not only by inhibiting the COX-2 enzyme but also by inhibiting the COX-1 enzyme (Masferrer et al., Proceedings of the National Academy of Sciences of the United States of America, 91:3228-3232, 1994; Seibert et al., Proceedings of the National Academy of Sciences of the United States of America, 91:12013-12017, 1994).

Specifically, macrophages activate nuclear factor-kB (NF-kB), which is a transcription factor of inflammatory responses, by stimulation such as cytokines, TNF-α, or lipopolysaccharides (LPS) and as a result, express inducible nitric oxide synthase (iNOS) and cyclooxygenase-2 (COX-2) to generate excess amounts of nitrogen monoxide (NO) and prostaglandin E2 (PGE2), thereby causing inflammation (Nishida T et al. Geranylgeranylacetone induces cyclooxygenase-2 expression in cultured rat gastric epithelial cells through NF-kappa B. Digestive Diseases and Sciences. 52: 1890-1896 (2007)).

Synthetic anti-inflammatory drugs developed so far may be broadly classified into steroids (hydrocortisone, prednisolone, and betamethasone) and non-steroids (aspirin, indomethacin, and ibuprofen), and most thereof exhibit side effects such as stomach, kidney and heart disease, and the like (Dagne J M, et al. Cardiovascular side-effects: from light to shadow. Currpharm Des. 12: 917-975 (2006) and Makins R, Ballinger A. Gastrointestinal side effects of drugs. Expert Opin Drug Saf. 2: 421-429 (2003)). Therefore, there is a need to develop a natural substance-derived anti-inflammatory therapeutic agent that is safer and more effective than existing therapeutic agents.

Technical Problem to be Solved

One object of the present invention to provide a black rice sprouting liquid having an excellent anti-inflammatory effect through low-temperature treatment and room-temperature treatment of water used when black rice is sprouted, and a manufacturing method of the black rice sprouting liquid.

BRIEF SUMMARY OF THE INVENTION

In accordance with one aspect of the present invention, provided is a black rice sprouting liquid having an anti-inflammatory effect, the black rice sprouting liquid being obtained by performing low-temperature treatment on water used when black rice is sprouted in an open container at a temperature ranging from 1° C. to 5° C. for 1 day to 10 days, and then performing room-temperature treatment on the resulting water in the open container at a temperature ranging from 10° C. to 30° C. for 30 days to 210 days.

In accordance with another aspect of the present invention, provided is a manufacturing method of a black rice sprouting liquid having an anti-inflammatory effect, the method including: (1) a black rice sprouting step of immersing black rice in water to sprout the black rice; (2) a sprouting liquid separation step of separating sprouted black rice from a sprouting liquid used when black rice is sprouted; (3) a low-temperature treatment step of performing low-temperature treatment on the sprouting liquid in an open container at a temperature ranging from 1° C. to 5° C. for 1 day to 10 days; and (4) performing room-temperature treatment on the low-temperature treated sprouting liquid in the open container at a temperature ranging from 10° C. to 30° C. for 30 days to 210 days.

Advantageous Effects

According to the present invention, there are provided a black rice sprouting liquid having an excellent anti-inflammatory effect through low-temperature treatment and room-temperature treatment of water used when black rice is sprouted, and a manufacturing method of the black rice sprouting liquid.

DESCRPTION OF DRAWINGS

FIG. 1 is a copy of a test report showing results of analyzing bacteria present in a black rice sprouting liquid before low-temperature treatment and room-temperature treatment.

FIGS. 4a to 8 are images showing experimental results of the antifungal activity of examples of the present invention.

DETAILED DESCRIPTION OF THE INVENTION

Hereinafter, the present invention will be described in detail with reference to specific embodiments.

A black rice sprouting liquid according to the present invention is characterized in that water used when black rice is sprouted is subjected to low-temperature treatment in an open container at a temperature ranging from 1° C. to 5° C. for 1 day to 10 days, and then is subjected to room-temperature treatment in the open container at a temperature ranging from 10° C. to 30° C. for 30 days to 210 days.

Rice, which belongs to the Gramineae family, is one of the world's three major grains, including wheat and corn, and is the most important food resource in the world. In addition, rice does not easily rot due to low moisture and protein contents and high carbohydrate content thereof, and therefore, is an important calorie source that is easily stored.

Anthocyanin contained in black rice is known to be effective in preventing cancer and enhancing immunity, in addition to having the aforementioned strong antioxidant effect. Black rice, which is a type of colored rice, is processed into various types of food due to unique color and flavor thereof, and consumption thereof is gradually increasing. It is reported that the scent of black rice is derived from alcohol components such as ethanediol and guaiacol, ketones such as hexadecanoic acid, hexanal, and acetic acid, aldehydes, and organic acids, and black rice contains, as main pigment components, glycosides such as cyanidin-3-glucoside (C3G) and peonidin-3-glucoside (P3G).

In particular, black rice contains, as pigment components, polyphenol compounds having various structures and molecular weights, and these polyphenol compounds have been confirmed to have physiological activities such as antioxidant, antimicrobial and anticancer properties. In addition, black rice is supplied as brown rice, has a higher dietary fiber content than that of ordinary brown rice, has unique flavor, and has high contents of protein, vitamin B, and minerals. According to the Compendium of Materia Medica, which is a Chinese pharmaceutical text written by Li Shizhen, black rice strengthens the kidneys, strengthens the stomach, and stimulates blood circulation, and is distinctly effective in preventing and treating dizziness, anemia, and gray hair, and diseases such as eye diseases, polyuria, constipation, and cardiovascular diseases.

When raw black rice is eaten every day, black rice is known to improve overall control functions of the human body and strengthen immune functions, thus being effective in preventing aging and diseases, enhancing beauty of women, and the like. Black rice is effective especially in anemia likely to occur in pregnant women, and the like, and is very helpful for the formation of bone in children. In addition, when infants eat black rice as a baby food, it is very helpful for infants to grow healthy. In addition, black rice has a high selenium (Se) content, and thus is effective in preventing cancer. In a Chinese document (November, 1992), there is a report of research on improvement of the condition of patients as a result of long-term intake of black rice in 40 patients with rectal cancer. In particular, a nutritional health food eaten as a porridge prepared by boiling black rice, adlay, jujubes, and the like has been passed down since ancient times, as a food that enables people who travel along the Silk Road of China or residents of Xinjiang province to beat the heat of the Taklamakan desert. In addition, black rice has a good color and a savory flavor, is effective in treating diabetes, constipation, gastrointestinal disorders, and the like, and is more abundant in vitamins B, C, and E than ordinary rice, and thus may be regarded as a healthy black grain food that is good for the human body.

Since black rice is used after being milled into brown rice, it has embryos, and thus contains larger amounts of many kinds of nutrients than ordinary rice, and black rice has a black chromaticity that is 5 times that of ordinary rice. It is known that black rice is very abundant in anthocyanin, which is a natural pigment, and the like, and very abundant in inorganic salts such as iron, zinc, selenium, and the like, as well as vitamin E, and thus has an excellent active oxygen-scavenging function. When people eat black rice, an effect of preventing skin aging may be anticipated due to antioxidant components contained in black rice in a remarkably large amount, such as anthocyanin and oryzafuran, which eliminate active oxygen. Black rice having these physiological and pharmacological effects is drawing attention in terms of a utility value thereof. Black rice is mainly produced in Southern Asia and China, and is currently produced in some regions in Korea, and is known to have a great medical effect. In particular, a purple pigment of black rice has high stability with respect to high temperature and sunlight, and thus black rice is used as a food ingredient in processed foods, such as bread, porridge, noodles, and the like.

Examples of the use of black rice as various food substances are as follows.

Korean Patent Registration No. 451126 discloses noodles made of black rice which includes, as main ingredients, 55 wt % to 70 wt % of rice flour obtained by grinding rice or black rice into 140 mesh to 180 mesh, 20 wt % to 28 wt % of white flour, 5 wt % to 8 wt % of edible salt, and 5 wt % to 10 wt % of water, and a method of producing the noodles.

Korean Patent Publication No. 2000-75359 discloses a rice cracker made of black rice, which is prepared by adding water to a rice mixture of black rice and brown rice such that a moisture content becomes 18%, and puffing the prepared dough, and a method of producing the rice cracker.

Korean Patent Publication No. 2002-92334 discloses black rice cake for a rice cake soup, which is produced by uniformly mixing a pulverized flour mixture of 1.5 L to 1.8 L of mineral water, 1.5 kg to 2.5 kg of black rice, 1.5 kg to 2.5 kg of barley, 6 kg to 7 kg of white rice, 400 g to 500 g of potato starch, and 0.4 g to 0.5 g of refined salt and steaming the resulting mixture using steam at 100° C. to 120° C.

Korean Patent Publication No. 2001-105020 discloses noodles including a vegetable extract prepared by mixing a vegetable with flour in a liquid or powder state, and kneading, rolling, and molding the resulting mixture, and a method of producing the noodles.

Korean Patent Publication No. 2002-42384 discloses black rice flour-added bread prepared by mixing black rice and flour in a certain ratio, mixing the resulting mixture with an appropriate amount of water, and kneading and fermenting the mixture, and a manufacturing method of the bread.

In the present invention, black rice is rich in anthocyanin and inorganic salts, and thus is known to effectively neutralize active oxygen in the body. For example, the black rice may be *Oryza sativa* cv. *Heugjinjubyeo* cultivated in Jindo, Korea. It has been reported that *Oryza sativa* cv. *Heugjinjubyeo* has a pericarp part with a deep purple color, and includes cyanidin and melvidin, which are anthocyanin compounds; glucosides thereof, such as cyanidin glucoside, melvidin glucoside, delphinidin glucoside, alkaloids, and phenol compounds; and 2-hydroxy-4-methoxypyridine. In addition, black rice is rich in minerals and thus has alkaline properties. Alkaline foods have an effect of preventing various inflammatory diseases by neutralizing the body oxidized by various pollutants and food oxides. In particular, black rice contains selenium in the largest amount among minerals, and it is known that selenium contained in black rice not only activates hepatocytes but also inhibits hepatocyte destruction.

Black rice may have a milling degree of 9 to 10. The degree of milling refers to an extent to which bran is removed, and indicates that, when a total thickness of the outer layer and the rice bran layer based on brown rice and white rice is divided into 10 equal parts, complete removal of these 10 equal parts is referred to as a milling degree of 10 and a state of brown rice in which the 10 equal parts are not completely removed is referred to as a milling degree of 0. Thus, a milling degree of 5 refers to a state in which about 50% of the outer layer and the rice bran layer is removed. The degree of milling is also expressed by weight, and generally, the weight of the outer layer and the rice bran layer accounts for about 8% to about 9% of a total weight of brown rice. This may not be applied equally to all types of rice since it varies depending on the kind of rice, but to facilitate milling, milling corresponding to 8% of a total weight is referred to as a milling degree of 10. In other words, a milling degree of 1 is referred to as milling corresponding to about 0.8% of a total weight of brown rice. It can be understood that rice having a milling degree of 5, which is called on the market, refers to rice milled by about 4% of the total weight of brown rice, and rice having a milling degree of 7 refers to rice milled by about 5.6% of the total weight of brown rice. As described above, when milling is performed at a milling degree of 9 or 10, rice bran required for sprouting remains and thus sprouting is possible.

The sprouting of black rice may be performed by immersing black rice in water at a temperature of 16° C. to 23° C. for 24 hours to 48 hours. The above temperature range may be understood as a room temperature condition corresponding to the winter season of the Republic of Korea.

The sprouting of black rice may be performed by immersing black rice in water at a temperature of 23° C. to 30° C. for 15 hours to 24 hours. The above temperature range may be understood as a room temperature condition corresponding to the summer season of the Republic of Korea.

The aforementioned sprouting temperature and sprouting time may be understood as appropriate conditions for sprouting of about 0.5 mm to about 1.5 mm from black rice.

During the sprouting of black rice, water is stirred, and preferably, a lower stream of water is lifted upward and an upper stream of water is again dropped downward. By stirring water, contamination of water due to stagnation is prevented. It is understood that water is purified due to contact with naturally generated magnetic force, oxygen, and the like while water flows without stagnating, thus preventing contamination of water, this may be understood as being the same as and/or similar to the fact that naturally flowing water has a higher self-purification capacity than that of stagnated water, and the stirring of water may be understood as a method applied to water treatment.

Water used during sprouting may be drinking water, and the use of tap water is possible.

Figure 2:
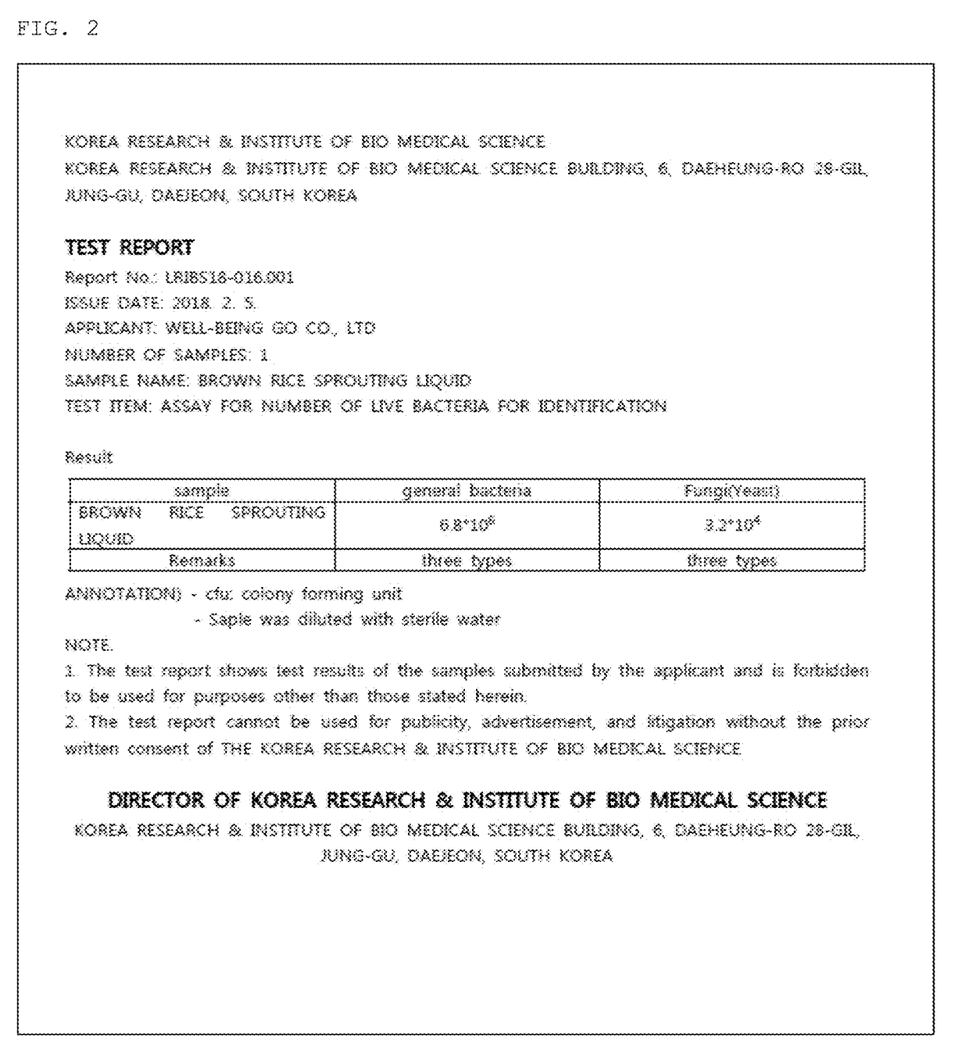
FIGS. 2 and 3 are copies of test reports showing results of analyzing bacteria present in a black rice sprouting liquid obtained after low-temperature treatment and room-temperature treatment, according to the present invention.
Figure 3:
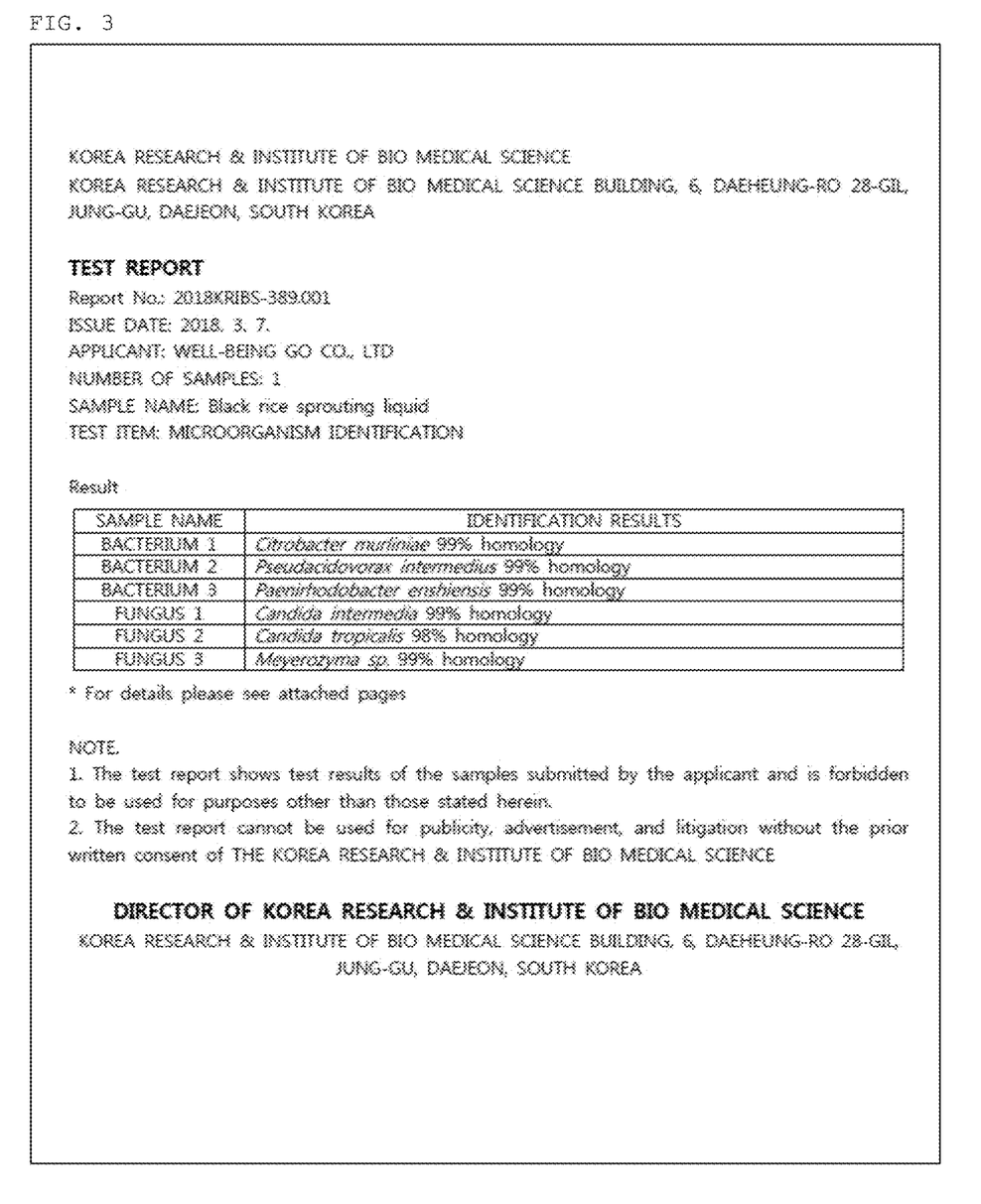

A sprouting liquid before low-temperature treatment and room-temperature treatment contains, as illustrated in FIG. 1, general bacteria at a density of 92,000,000 CFU/g and *E. coli* at a density of 1,100,000 CFU/g, whereas the sprouting liquid after low-temperature treatment and room-temperature treatment, according to the present invention, particularly contains three types of general bacteria and three types of fungi as shown in a test report of FIG. 2, and as illustrated in FIG. 3, it was confirmed that *Citrobacter murliniae, Pseudacidovorax intermedius*, and *Paenirhodobacter enshiensis* were present as the general bacteria, and *Candida intermedia, Candida tropicalis*, and *Meyerzyma* sp. were present as the fungi.

The present invention also provides a manufacturing method of a black rice sprouting liquid, including: (1) a black rice sprouting step of immersing black rice in water to sprout the black rice; (2) a sprouting liquid separation step of separating the sprouted black rice from the sprouting liquid used when black rice is sprouted; (3) a low-temperature treatment step of performing low-temperature treatment on the sprouting liquid in an open container at a temperature ranging from 1° C. to 5° C. for 1 day to 10 days; and (4) performing room-temperature treatment on the low-temperature treated sprouting liquid in the open container at a temperature ranging from 10° C. to 30° C. for 30 days to 210 days.

The black rice sprouting step of above (1) includes immersing black rice in water to sprout the black rice. Contents of black rice and the black rice sprouting liquid may be understood as being the same as and/or similar to those described above. Sprouting of seeds requires an appropriate temperature determined for each of seeds of a plant, sufficient oxygen, and appropriate moisture, and particularly, there are those requiring light and those requiring darkness according to the species of plant, but most plants have no relation to the presence or absence of light. When sprouting is started, various enzymes start to act, and respiratory activity becomes active and storage nutrients are decomposed and converted into easy-to-use forms. In addition, this is used in rapid activity of divisive tissues such as young buds, radicles, and the like. Storage nutrients in seeds are in the form of starch, fat, protein, and the like, and are contained in endosperms (the Gramineae family, and the like), perisperms (lotus and the like), and cotyledons (legume family and the like). As sprouting progresses, the storage nutrients are reduced, but chlorophyll is formed in cotyledons, primary leaves, and the like, and thus photosynthesis gradually occurs and roots also absorb nutrients and moisture, so that plants grow by themselves independently of nutrients, not through growth dependent on the storage nutrients. Thus, new components that have not been present before sprouting may be produced.

The sprouting liquid separation step of above (2) includes separating sprouted black rice produced by the black rice sprouting step of above (1) from a sprouting liquid used when black rice is sprouted. The sprouted black rice may be used in rice cooking and the like alone or in combination with other types of rice. When rice cooking is performed using sprouted black rice, the cooked black rice exhibits high digestibility. The present invention is characterized in that sprouted black rice is used in accordance with the original purpose, and a sprouting liquid that may be obtained as a byproduct is utilized. That is, the present invention is characterized in that water supplied to sprout black rice is recovered into a sprouting liquid as a byproduct after black rice is sprouted, and the sprouting liquid is utilized. The obtained sprouting liquid has a black color. This is considered that identified or unidentified many effective physiologically active substances, including especially anthocyanin contained in black rice in a large amount, are eluted.

The low-temperature treatment step of above (3) includes performing low-temperature treatment on the sprouting liquid obtained by the sprouting liquid separation step of above (2), in an open container at a temperature ranging from 1° C. to 5° C. for 1 day to 10 days. The sprouting liquid before and after such low-temperature treatment has a pH of 4.5 to 5.5.

The room-temperature treatment step of above (4) includes performing room-temperature treatment on the sprouting liquid having undergone the low-temperature treatment step of above (3), in the open container at a temperature ranging from 10° C. to 30° C. for 30 days to 210 days. The pH of the sprouting liquid after room-temperature treatment is increased to 7.5 to 8.

Black rice may have a milling degree of 9 to 10. Contents related to the degree of milling may be understood as being the same as and/or similar to those described above.

The sprouting of black rice may be performed by immersing black rice in flowing water at a temperature of 16° C. to 23° C. for 24 hours to 48 hours. The above temperature range may be understood as a room temperature condition corresponding to the winter season of the Republic of Korea.

The sprouting of black rice may be performed by immersing black rice in flowing water at a temperature of 23° C. to 30° C. for 15 hours to 24 hours. The above temperature range may be understood as a room temperature condition corresponding to the summer season of the Republic of Korea.

The aforementioned sprouting temperature and sprouting time may be understood as appropriate conditions for sprouting of black rice by about 0.5 mm to about 1.5 mm.

When black rice is sprouted, water may be stirred. By stirring water, contamination of water due to stagnation is prevented.

Water used during sprouting may be drinking water, and the use of tap water is possible.

Hereinafter, the present invention will be described with reference to the following examples and comparative examples.

These examples are provided for illustrative purposes only and are not intended to limit the scope of the present invention.

Examples 1 and 2

5 L of general tap water was poured into 500 g of black rice milled at a milling degree of about 9, and the black rice was sprouted at a temperature of 20° C.±3° C. for about 15 hours to about 48 hours while being stirred to obtain sprouted black rice and a sprouting liquid, the sprouting liquid with a black color was separated from the sprouted black rice, the separated sprouting liquid was poured into an open container, the pH of the sprouting liquid was measured (at this time, pH=about 5.5; this is referred to as "Example 1"), followed by low-temperature treatment in a refrigerator, a temperature of which was maintained at 2° C.±0.1° C., for hours. After low-temperature treatment, the sprouting liquid was subjected to room-temperature treatment at room temperature (a temperature of about 20° C.±3° C.) for 50 days in a state in which the solution was accommodated in the open container. After the room-temperature treatment, the pH of the sprouting liquid was measured, and as a result, the pH of the sprouting liquid was about 7.8 (this is referred to as "Example 2").

As a result of measuring bacteria present in the obtained black rice sprouting liquid according to the present invention, it was confirmed that, as illustrated in FIGS. 2 and 3, the black rice sprouting liquid included three types of general bacteria and three types of fungi, and, as illustrated in FIG. 3, *Citrobacter murliniae, Pseudacidovorax intermedius*, and *Paenirhodobacter enshiensis* were present as the general bacteria, and *Candida intermedia, Candida tropicalis*, and *Meyerzyma* sp. were present as the fungi.

For convenience of storage and use, the black rice sprouting liquids of Examples 1 and 2 were filtered through paper, lyophilized, powdered, and stored, and were diluted in distilled water immediately before use.

Comparative Example 1

A sprouted brown rice solution was prepared in the same manner as in the above examples, except that brown rice milled at a milling degree of about 9 was used instead of the black rice milled at a milling degree of about 9, but it was frequently confirmed that the black rice sprouting liquid was decayed during low-temperature treatment and room-temperature treatment, thus causing an odor.

Comparative Example 2

A black rice sprouting liquid was prepared in the same manner as in the above examples, except that black rice milled at a milling degree of about 9 having not undergone low-temperature treatment was used, but it was confirmed that, since the black rice sprouting liquid had not undergone low-temperature treatment, it decayed during room-temperature treatment, thus causing an odor.

Comparative Example 3

Sprouting was performed using black rice milled at a milling degree of about 9 in the same manner as in the above examples to obtain a sprouting liquid, except that, after sprouting, low-temperature treatment and room-temperature treatment were not performed. An initial pH of the obtained black rice sprouting liquid was about 4.5, and it was confirmed that general bacteria were present at a density of 92,000,000 CFU/g, and *E. coli* was present at a density of 1,100,000 CFU/g.

Experimental Example 1: Experiment for Antifungal Activity (1)

1. Experimental Bacteria

*Trichophyton rubrum* (KCTC 6375), which is a type of fungus known as a causative bacterium of tinea pedis, was distributed from Daegu Medical University and activated by sub-culturing three times or more before being used in the experiment for antifungal activity, and then was used in the experiment.

2. Used Medium

To confirm growth patterns, sub-culturing, and antifungal activity, Sabouraud dextrose agar (SDA) was used.

3. Antifungal Activity Verification (Paper Disc Agar Diffusion Method)

Antifungal activity was verified using a paper disc agar diffusion method. A test strain was collected with a Cork borer (5 mm) and placed at the center of a medium, a paper disc was attached to the medium such that the test strain was not separated therefrom, and then 50 µl of a sample including each of the black rice sprouting liquids of Examples 1 and 2 at concentrations (solid content) of 5 mg/ml and 10 mg/ml, respectively, was injected into a culture apparatus, followed by culturing at 25° C. for 7 days or longer, and then it was confirmed whether a growth inhibition zone was generated. To examine the effect of sprouted black rice powder (solids), sterilized water was used as a control.

Figure 4A:
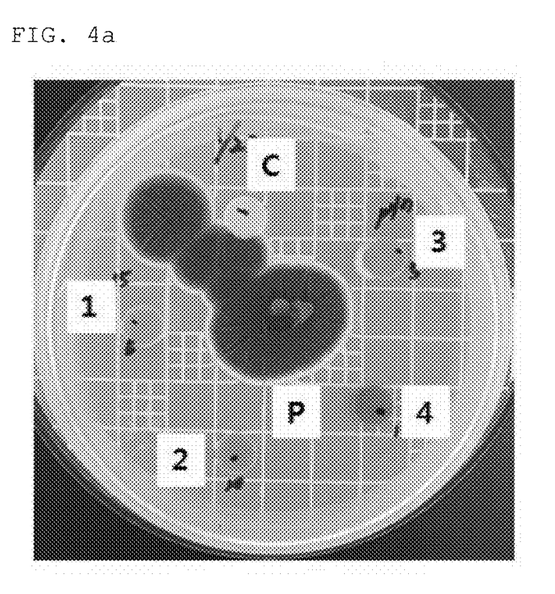
Figure 4B:
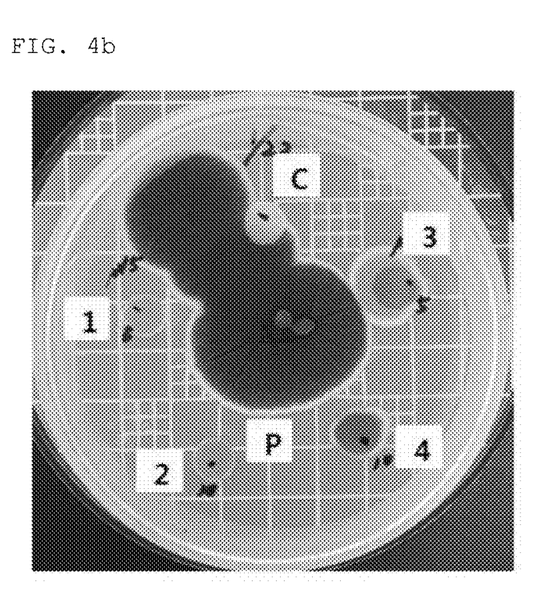

Results of testing the antifungal activity of each of the samples including the solutions of Examples 1 and 2 at concentrations of 5 mg/ml and 10 mg/ml, respectively, through a paper disc agar diffusion assay are shown in FIG. 4 and Table 1. As a result of the experiment, after 5 days, inhibition of the growth of *Trichophyton rubrum* (KCTC 6375) was shown, i.e., 80 mm and 150 mm at 5 mg/ml and 10 mg/ml, respectively for the case of Example 1, and 70 mm and 140 mm at 5 mg/ml and 10 mg/ml, respectively for the case of Example (see FIG. 4A), and after 7 days, the cases of Examples 1 and 2 exhibited similar antifungal activities, i.e., 70 mm and 130 mm at 5 mg/ml and 10 mg/ml, respectively, for the case of Example 1 and 50 mm and 110 mm at 5 mg/ml and 10 mg/ml, respectively, for the case of Example 2 (see FIG. 4B).

TABLE 1

| | Example 1 | | | |
| --- | --- | --- | --- | --- |
| | After 5 days | | After 7 days | |
| Strain | 5 mg/ml | 10 mg/ml | 5 mg/ml | 10 mg/ml |
| *Trichophyton rubrum* KCTC 6375 | 80 | 150 | 70 | 140 |
| | Example 2 | | | |
| | After 5 days | | After 5 days | |
| Strain | 5 mg/ml | 10 mg/ml | 5 mg/ml | 10 mg/ml |
| *Trichophyton rubrum* KCTC 6375 | 70 | 130 | 50 | 110 |

Growth inhibition: mm

Figure 4C:
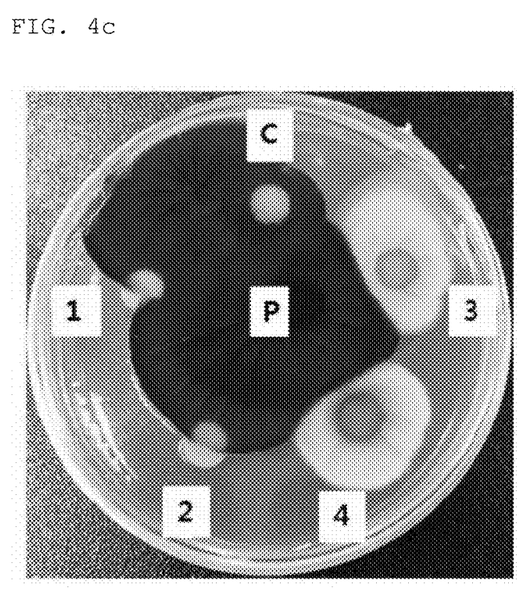

In FIG. 4, P denotes a strain (*Trichophyton rubrum* KCTC 6375); C denotes distilled water as a control; 1 denotes 5 mg/ml (Example 1); 2 denotes 10 mg/ml (Example 1); 3 denotes 5 mg/ml (Example 2); and 4 denotes 10 mg/ml (Example 2).

Experimental Example 2: Experiment for Antifungal Activity (2)

The culturing step of Experimental Example 1 was performed for an extended period of time, i.e., 10 days or longer. As a result of the experiment, it was confirmed that, after 10 days or more of culture, growth of an unknown white fungus occurred in Example 2, and it was confirmed that, due to the antifungal activity of the unknown fungus, as illustrated in Table 2 below and FIG. 4C, the growth of the tinea pedis fungus (*Trichophyton rubrum*) was considerably inhibited.

TABLE 2

| Strain | Example 1<br>5 mg/ml | Example 2<br>5 mg/ml |
|---|---|---|
| *Trichophyton rubrum* KCTC 6375 | +++ | + |

+++, No inhibition;
++, Mild inhibition;
+, Moderate inhibition

Figure 5:
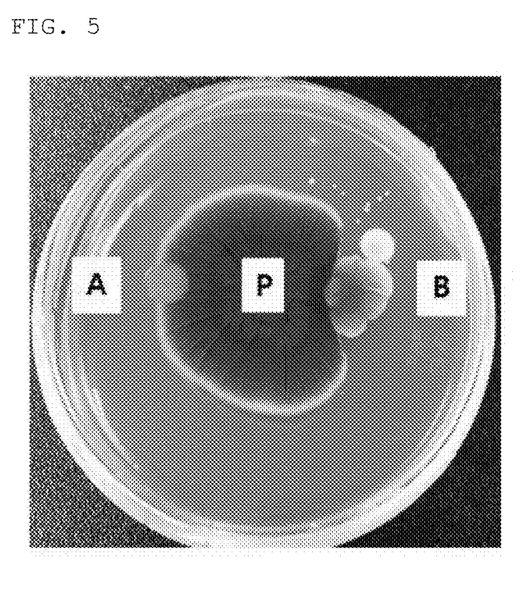

Results of confirming unknown white fungi observed in Example 2 and results of performing an experiment on the cases of Examples 1 and 2 according to concentrations, i.e., 5 mg/ml and 10 mg/ml are shown in Table 3 and FIG. 5. It was confirmed that, while the unknown white fungus was still not observed in Example 1, the growth of the unknown white fungus occurred in Example 2, and the concentration of the unknown fungus was significantly increased with respect to a concentration difference between 5 mg/ml and 10 mg/ml.

TABLE 3

| Strain | Example 1 | | Example 2 | |
|---|---|---|---|---|
| | 5 mg/ml | 10 mg/ml | 5 mg/ml | 10 mg/ml |
| *Trichophyton rubrum* KCTC 6375 | +++ | +++ | + | + |

+++, No inhibition;
++, Mild inhibition;
+, Moderate inhibition

In FIG. 5, P denotes a strain (*Trichophyton rubrum*); C denotes distilled water as a control; 1 denotes 5 mg/ml (Example 1); 2 denotes 10 mg/ml (Example 1); 3 denotes 5 mg/ml (Example 2); and 4 denotes 10 mg/ml (Example 2).

Figure 6:
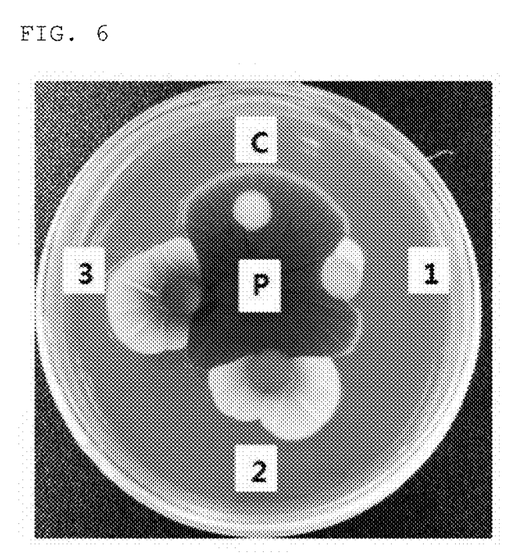

In addition, to examine a significant correlation between the unknown white fungus found in Example 2 and concentrations, an experiment was carried out on the case of Example 2 according to concentrations, i.e., 1 mg/ml, 5 mg/ml, and 10 mg/ml, and results thereof are shown in Table 4 and FIG. 6.

As a result, it was confirmed that, as the concentration in Example 2 was increased, the concentration of the unknown white fungus and the antifungal activity of the tinea pedis fungus (*Trichophyton rubrum*) were also relatively increased.

TABLE 4

| Strain | Example 2 | | |
|---|---|---|---|
| | 1 mg/ml | 5 mg/ml | 10 mg/ml |
| *Trichophyton rubrum* KCTC 6375 | ++ | + | + |

+++, No inhibition;
++, Mild inhibition;
+, Moderate inhibition

In FIG. 6, P denotes a strain (*Trichophyton rubrum*); C denotes distilled water as a control; 1 denotes 1 mg/ml (Example 2); 2 denotes 5 mg/ml (Example 2); and 3 denotes 10 mg/ml (Example 2).

As a result of the experiment, it was confirmed that the growth of the tinea pedis fungus (*Trichophyton rubrum*) was inhibited due to the antifungal activity of each of the cases of Examples 1 and 2 after 5 days, and the cases of Examples 1 and 2 exhibited similar activities after 7 days.

Experimental Example 3: Experiment for Antifungal Activity (3)

Figure 7:
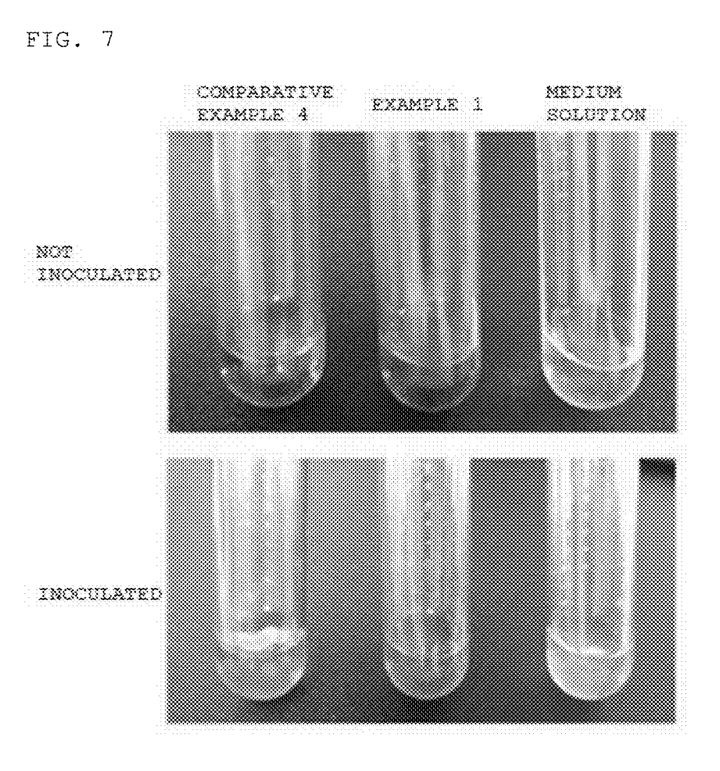
Figure 8:
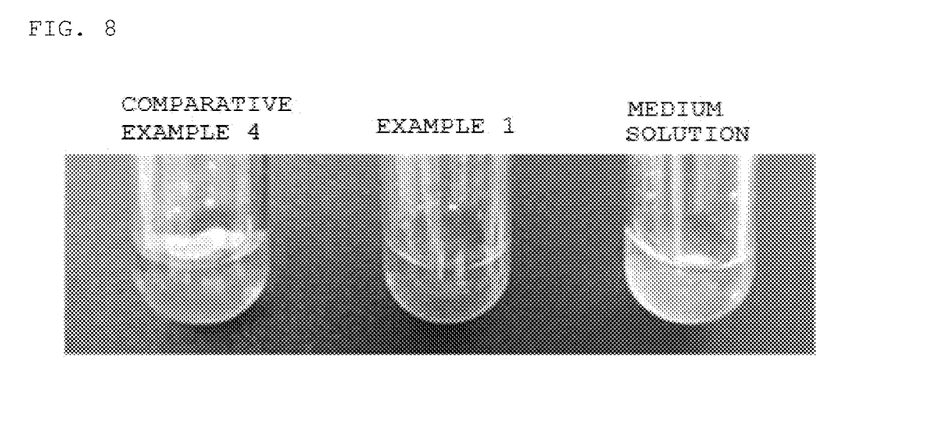

An antimicrobial effect of the black rice sprouting liquid on *Trichophyton rubrum* (KCTC6375), which is a tinea pedis fungus, was measured using the method of Chandrasekaran and Venkatesalu (Journal of Ethnopharmacology, 91, 105-108 (2004)). The strain was cultured in Sabouraud dextrose broth at 28° C. for 3 days, and then diluted in a medium such that absorbance at 450 nm reached 0.6. 1 ml of the medium including the extract was inoculated with 50 µl of each bacterial dilute. At this time, the extract was prepared into a 2-fold dilution series such that concentrations of the extract in the medium were 10%, 20%, and 40%. After incubation at 28° C. for 3 days, it was observed whether the bacterium was grown, and the results thereof are shown in FIGS. 7 and 8. FIG. 8 is an enlarged image of FIG. 7.

As illustrated in FIGS. 7 and 8, a tinea pedis suspension was confirmed in Comparative Example 4 (non-sprouting liquid obtained by pouring 5 L of general tap water into 500 g of black rice milled at a milling degree of about 7 and immersing the black rice in the water at a temperature of 20° C.±3° C. for about 24 hours while being slowly stirred) and a medium solution, and a tinea pedis suspension was not confirmed in Example 1, and thus 40% was confirmed as a minimum inhibitory concentration (MIC).

Experimental Example 4: Experiment for Antiviral Activity

The black rice sprouting liquid of Example 1 was used in an experiment for antiviral activity.

The antiviral activity of each of the cases of Comparative Example 4 and Example 1 against herpes simplex virus (HSV) was tested using Vero cells as follows.

Vero cells ($1 \times 10^3$ cells/well) were seeded into a 24-well TC plate, and then after 18 hours to 20 hours, 100 µg/ml or 200 µg/ml of each of the cases of Comparative Example 4 and Example 1 and HSV-1 (MOI: 2) were incubated together at ° C. for 1 hour, and then the Vero cells were inoculated therewith. 2 hours after inoculation of HSV-1 along with each of the cases of Comparative Example 4 and Example 1, the inoculation solution was removed from the Vero cells, followed by washing three times with PBS and replacement with 10% FBS-supplemented DMEM. A group treated only with 10% FBS-supplemented DMEM was used as a negative control. After 48 hours, the degree of viral infection was measured using a microscope. In addition, to measure cell viability, the cells were treated with 20 µl of MTT reagent and cultured for 1 hour, and absorbance at 450 nm was measured.

Analysis results of antiviral activity on herpes simplex virus using images of 48 hours after viral infection are as follows. As can be seen from FIGS. 9 and 10, it was confirmed that the viral infection rate was significantly reduced in cells treated with the black rice sprouting liquid after being infected with herpes simplex virus (see FIG. 9), and this case also exhibited cell viability that was 5 times or higher than that of the case of Comparative Example 4 and the virus-infected group.

Figure 9:
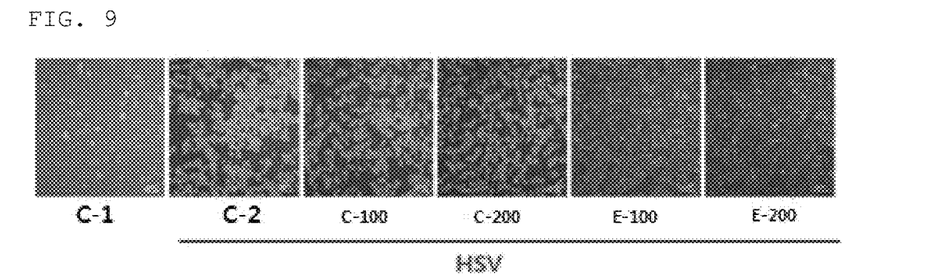
FIGS. 9 and 10 are images showing experimental results of the antiviral activity of examples of the present invention.
Figure 10:
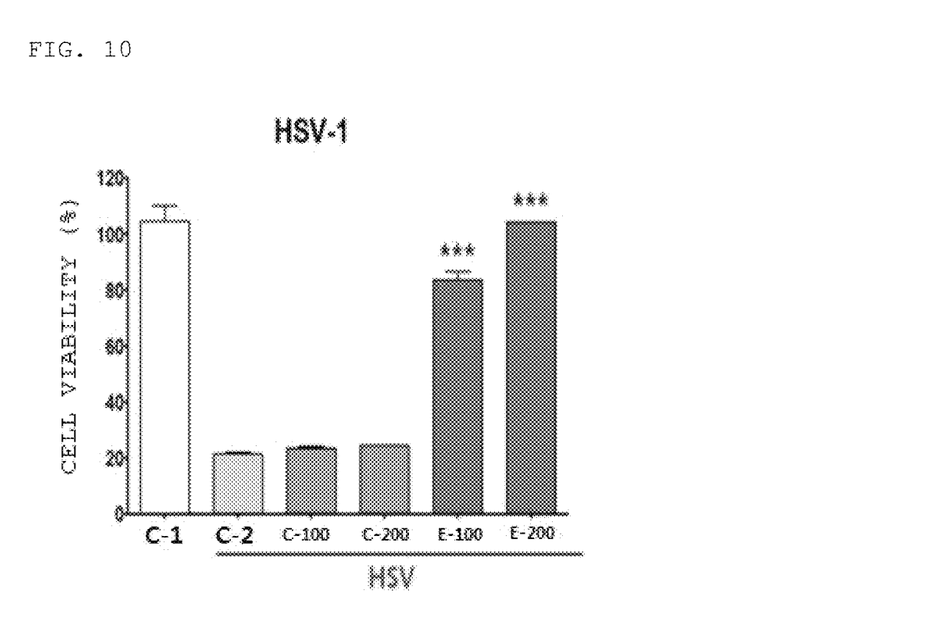

In FIGS. 9 and 10, C-1 denotes Vero cells (non-infected group), C-2 denotes Vero cells (HSV-infected group), C-100 denotes Comparative Example 4 (concentration: 100 µg/ml), C-200 denotes Comparative Example 4 (concentration: 200

μg/ml), E-100 denotes Example 1 (concentration: 100 μg/ml), and E-200 denotes Example 1 (concentration: 200 μg/ml).

In the case of Comparative Examples 1 and 2, a usable sprouting liquid to be applied to an experiment was not obtained due to decay thereof, and in the case of Comparative Example 3, an initial bacterial state and a pH change state were confirmed using the black rice sprouting liquid obtained in the same manner as that described above.

While the present invention has been described in detail with reference to particular embodiments, it will be obvious to those of ordinary skill in the art that various changes and modifications may be made within the spirit and scope of the present invention, and these changes and modifications are also within the scope of the appended claims.

DESCRIPTION OF REFERENCE NUMERALS (No reference numerals)

The invention claimed is:

1. A manufacturing method of a black rice sprouting liquid having an anti-inflammatory effect, the method comprising:
   (1) a black rice sprouting step of immersing black rice in water to sprout the black rice;
   (2) a sprouting liquid separation step of separating sprouted black rice from a sprouting liquid used when black rice is sprouted;
   (3) a low-temperature treatment step of performing low-temperature treatment on the sprouting liquid in an open container at a temperature ranging from 1° C. to 5° C. for 1 day to 10 days; and
   (4) performing room-temperature treatment on the low-temperature treated sprouting liquid in the open container at a temperature ranging from 10° C. to 30° C. for 30 days to 210 days,
   wherein a pH ranging from 4.5 to 5.5 before, during, or after the low-temperature treatment is increased to a pH ranging from 7.5 to 8 after the room-temperature treatment.

2. The method according to claim 1, wherein the sprouting of the black rice is performed by immersion in water at 23° C. to 30° C. for 15 hours to 24 hours.

3. The method according to claim 1, wherein the sprouting of the black rice is performed by immersion in water at 16° C. to 23° C. for 24 hours to 48 hours.

4. The method according to claim 1, wherein, when black rice is sprouted, the water is stirred.

* * * * *